US005609153A

United States Patent [19]
Dumoulin et al.

[11] Patent Number: 5,609,153
[45] Date of Patent: *Mar. 11, 1997

[54] MAGNETIC RESONANCE (MR) ANGIOGRAPHY USING A TOROIDAL POLARIZING MAGNET AND A LOW-FIELD IMAGING MAGNET

[75] Inventors: Charles L. Dumoulin, Ballston Lake; Robert D. Darrow, Scotia, both of N.Y.

[73] Assignee: General Electric Company, Schenectady, N.Y.

[*] Notice: The term of this patent shall not extend beyond the expiration date of Pat. No. 5,479,925.

[21] Appl. No.: 534,998

[22] Filed: Sep. 27, 1995

[51] Int. Cl.⁶ .................................................... A61B 5/055
[52] U.S. Cl. .................................. 128/653.2; 128/653.3; 128/653.4; 324/309
[58] Field of Search ............................. 128/653.2, 653.3, 128/653.4; 324/307, 309, 306

[56] References Cited

U.S. PATENT DOCUMENTS 5,447,156  9/1995  Dumoulin et al. .
5,479,925  1/1996  Dumoulin et al. .

*Primary Examiner*—Marvin M. Lateef
*Assistant Examiner*—Shawna J. Shaw
*Attorney, Agent, or Firm*—Lawrence P. Zale; Marvin Snyder

[57] ABSTRACT

A magnetic resonance (MR) active invasive device system employs a small, high-field polarizing magnet having a toroidal geometry, and a large low-field magnetic resonance (MR) imaging magnet for the purpose of generating MR angiograms of selected blood vessels. A subject is positioned in a large low-field MR imaging magnet. A catheter is inserted into the patient at or near the root of a vessel tree to be imaged. A fluid, intended to be used as a contrast agent is first passed through the small high-field polarizing magnet, causing a great deal of net longitudinal magnetization to be produced in the fluid. The fluid is then introduced into the subject through the catheter. Radiofrequency (RF) pulses and magnetic field gradients are then applied to the patient as in conventional MR imaging. Since the fluid has a larger longitudinal magnetization, before the MR imaging sequence, the fluid produces a much larger MR response signal than other tissue, resulting in the vessel tree being imaged with excellent contrast.

2 Claims, 3 Drawing Sheets

MAGNETIC RESONANCE (MR) ANGIOGRAPHY USING A TOROIDAL POLARIZING MAGNET AND A LOW-FIELD IMAGING MAGNET

CROSS REFERENCES TO RELATED APPLICATIONS

This application is also related to U.S. Patent applications "MAGNETIC RESONANCE (MR) ANGIOGRAPHY USING AN INTEGRATED POLARIZING AND IMAGING MAGNET" by C. Dumoulin and S. Souza (Atty. Docket No. RD-23,708); "APPARATUS AND METHODS FOR MAGNETIC RESONANCE (MR) ANGIOGRAPHY USING HYDROGEN POLARIZED AT LOW TEMPERATURES" by S. Souza and C. Dumoulin (Atty. Docket No. RD-23,709); "APPARATUS AND METHODS FOR MAGNETIC RESONANCE (MR) ANGIOGRAPHY USING FLUIDS POLARIZED AT LOW TEMPERATURES" by C. Dumoulin, S. Souza and R. Darrow (Atty. Docket No. RD23,710); "APPARATUS AND METHODS FOR MAGNETIC RESONANCE (MR) IMAGING OF CAVITIES USING FLUIDS POLARIZED AT LOW TEMPERATURES" by S. Souza, C. Dumoulin, R. Darrow and H. Cline (Atty. Docket No. RD-23,714 and RD-24,258); and "MAGNETIC RESONANCE (MR) PERFUSION IMAGING IN A LOW-FIELD IMAGING MAGNET" by C. Dumoulin and S. Souza (Atty. Docket No. RD-23,778); all assigned to the present assignee, and all incorporated by reference.

BACKGROUND OF THE INVENTION

1. Field of the Invention

The present invention relates to medical imaging of blood vessels, and more particularly concerns the use of magnetic resonance to obtain such imaging.

2. Description of Related Art

Angiography, or the imaging of vascular structures, is very useful in diagnostic and therapeutic medical procedures. MR angiography is performed with a variety of methods, all of which rely on one of two basic phenomena. The first phenomena arises from changes in longitudinal spin magnetization as blood moves from one region of the patient to another. Methods that make use of this phenomenon have become known as "in-flow" or "time-off-light" methods. A commonly used time-of-flight method is threedimensional time-of-flight angiography. With this method, a region of interest is imaged with a relatively short repetition time, TR, and a relatively strong excitation radio-frequency (RF) pulse. This causes the MR spins within the field-of-view to become saturated and give weak MR response signals. Blood flowing into the field-of-view, however, enters in a fully relaxed state. Consequently, this blood gives a relatively strong MR response signal, until it too becomes saturated.

Because of the nature of blood vessel detection with time-of-flight methods, the stationary tissue surrounding the vessel cannot be completely suppressed. In addition, slowly moving blood, and blood that has been in the imaged volume for too long, becomes saturated and is poorly imaged.

A second type of MR angiography is based on the induction of phase shifts in transverse spin magnetization. These phase shifts are directly proportional to velocity and are induced by flow-encoding magnetic field gradient pulses. Phase-sensitive MR angiography methods exploit these phase shifts to create images in which the pixel intensity is a function of blood velocity. While phase-sensitive MR angiography can easily detect slow flow in complicated vessel geometries, it will also detect any moving tissue within the field-of-view. Consequently, phase-sensitive MR angiograms of the heart have artifacts arising from the moving heart muscle and from the moving pools of blood in the heart chambers.

In conventional MR imaging, an inhomogeneity of the static magnetic field produced by the main magnet causes distortion in the image. Therefore a main magnet having homogeneity over a large region is desirable.

Also, a stronger static magnetic field created by the main magnet yields a better signal to noise ratio, all other factors being equal. Typically, these main magnets have been constructed of a superconducting material requiring very low temperatures, and all related support apparatus. These magnets become very expensive.

There is also the problem of shielding a large high-field magnet. Entire shielding rooms have been constructed to reduce the effects of the magnetic field on nearby areas and equipment. Shielding is also a problem for smaller polarizing magnets since the polarizing magnet must be located close to the imaging magnet and the attractive force between the two magnets should be minimized.

Currently, there is a need for a system for obtaining high quality angiograms of a selected vessel without the problems incurred with unshielded high-field magnets.

SUMMARY OF THE INVENTION

A fluid is passed through a small high-field polarizing magnet having a toroid geometry before it is injected into a catheter inserted in a vessel of a patient. The toroidal geometry of the polarizing magnet minimizes the fringe fields generated by the magnet and consequently, permits the polarizing magnet to be placed relatively close to a nearby magnetic resonance imaging system. In order to achieve maximum polarization the fluid is made to reside in the polarizing field longer than several T1 periods. The polarized fluid is then rapidly injected into the patient. MR images are created of the polarized fluid with the MR system which comprises radio-frequency and magnetic field gradient coils and a less powerful static field imaging magnet. The overall system requires much less power to function than a conventional high-field imaging system, and employs a simpler, less expensive static imaging magnet which may be a resistive or permanent magnet instead of a superconducting magnet.

OBJECTS OF THE INVENTION

It is an object of the present invention to provide a system for imaging selected blood vessels using magnetic resonance without the need for a homogeneous high-field imaging magnet.

It is another object of the present invention to provide an MR angiography system which uses a polarizing magnet with minimal fringe fields.

It is another object of the present invention to provide an MR imaging system which may use an inexpensive resistive magnet for imaging.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

DETAILED DESCRIPTION OF THE INVENTION

Figure 1:
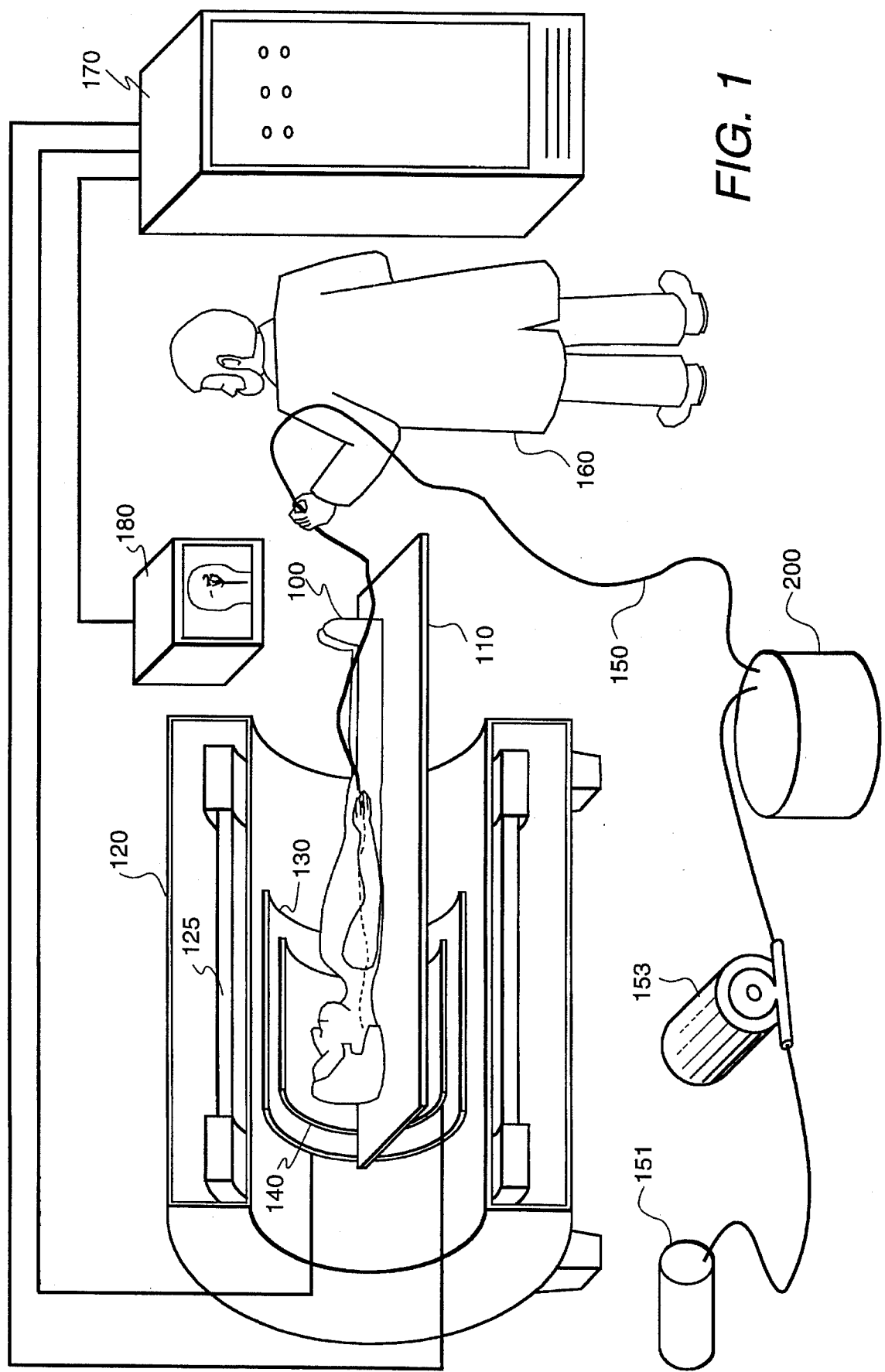
FIG. 1 is a perspective view of a first embodiment of the present invention in operation in which a vessel selective angiogram is being obtained from a subject.

In FIG. 1, a subject 100 is placed on a support table 110 and positioned in a homogeneous magnetic field generated by a magnet 125 encased in a magnet housing 120. In this embodiment, magnet 125 and magnet housing 120 have cylindrical symmetry and are shown sectioned in half to reveal the position of subject 100. Subject 100 is positioned such that a region of interest of subject 100 is located in the approximate center of the bore of magnet 125. Subject 100 is surrounded by a set of cylindrical magnetic field gradient coils 130 which create magnetic field gradients of predetermined strength at predetermined times according to predetermined MR pulse sequences, described later. Gradient coils 130 are capable of generating pulsed magnetic field gradients in three mutually orthogonal directions. At least one radio-frequency (RF) coil 140 (only one is shown in FIG. 1) also surrounds the region of interest of subject 100. In FIG. 1, RF coil 140 has a cylindrical shape with a diameter sufficient to encompass the entire subject. Other geometries, such as smaller cylinders specifically designed for imaging the head or an extremity, can be used in alternative embodiments. Non-cylindrical RF coils, such as surface coils, may also be used. RF coil 140 radiates radio-frequency energy into subject 100 at predetermined times and with sufficient power at a predetermined frequency so as to nutate a population of nuclear magnetic spins, hereinafter referred to as 'spins', of subject 100 in a fashion well known to those skilled in the art. RF coil 140 can also act as a receiver, detecting the MR response signals which are stimulated by nutation, if desired.

The nutation of the spins causes them to resonate at the Larmor frequency. The Larmor frequency for each spin is directly proportional to the strength of the magnetic field experienced by the spin. This field strength is the sum of the static magnetic field generated by magnet 125 and the local field generated by magnetic field gradient coil 130.

Fluid in a fluid reservoir 151 is passed through a toroidal polarizing magnet 200 by a pump 153, if required.

Toroidal polarizing magnet 200 is a superconducting magnet operating with relatively poor homogeneity if desired, but as high a field as possible. Designs in which the field strength approaches 15 Tesla or more are possible. Because of the toroidal geometry of the magnet, it is well shielded and has ideally no stray magnetic fields which can disturb the surrounding environment. The toroidal geometry creates a relatively uniform magnetic field within toroidal polarizing magnet 200. Since high homogeneity and large volume are not necessary for the present invention, toroidal polarizing magnet 200 should be considerably less expensive than magnets currently used in existing MR imaging systems.

Once the fluid is polarized in toroidal polarizing magnet 200, the polarized fluid is then injected through catheter 150 into subject 100 where it is imaged using conventional MR imaging methods.

The fluid which is injected into the subject 100 through catheter 150 should have the highest amount of polarization possible once it reaches the vessels. Consequently, the polarizing field of toroidal polarizing magnet 200 should be high. Also, the fluid will have to remain in the polarizing field for a period of time greater than five times the T1 of the fluid to reach full magnetization. Once the fluid leaves toroidal polarizing magnet 200 it will begin to lose polarization with a half-life equal to its T1. Consequently, it is desirable to deliver the fluid to the patient as quickly as possible. This can be done by minimizing the length of the catheter and maximizing the flow velocity.

The fluid in fluid reservoir 151 should have a T1 chosen to be as long as possible to maximize the amount of polarization delivered into the vessels of the patient. Possible choices of fluid are:

1) physiological saline solution;
2) blood previously obtained from the patient;
3) whole blood or plasma from a donor;
4) a blood substitute such as fluorinated hydrocarbons capable of carrying oxygen to tissue; and
5) blood recirculated from the patient.

Figure 2:
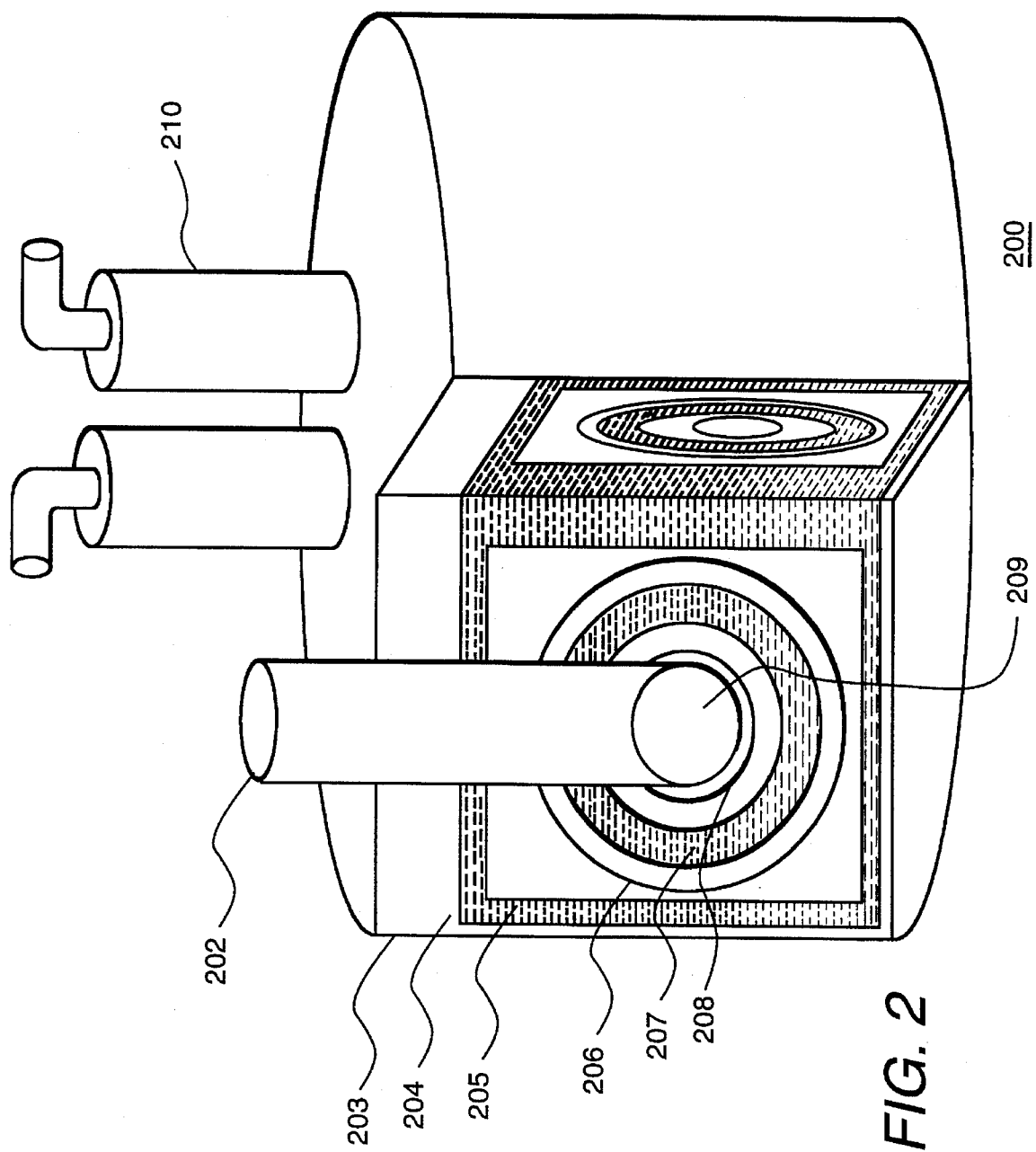
FIG. 2 is a cut-away perspective rendering of a polarizing magnet having a toroidal geometry.

FIG. 2 shows a cross-sectional view of one embodiment of toroidal polarizing magnet 200. Toroidal polarizing magnet 200 is constructed with a cylindrical outer case 203 (although other geometries are possible). Outer case 203 encloses a vacuum chamber 204 in which a liquid nitrogen cryostat 205 is suspended. Liquid nitrogen cryostat 205 surrounds an external radiation shield 206 which, in turn, surrounds a helium cryostat 207 in the which superconducting windings of toroidal polarizing magnet 200 are placed. External radiation shield 206 and helium cryostat 207 are each surrounded by a vacuum to minimize the transfer of heat into the cryostats.

Cryogenic gasses, electrical power and monitoring leads are introduced into the outer case through a stack 210. If desired, additional stacks 210 can be used to provide additional or alternative access for cryogenic gasses, electrical power and/or monitoring leads.

The fluid which is to be polarized is introduced into toroidal polarizing magnet 200 through an access port 202. Access port 202 provides a room temperature path to a room temperature magnet bore 209 where the magnetic field is contained. Heat transfer from room temperature magnet bore 209 into helium cryostat 207 is minimized by an internal radiation shield 208, as is common in conventional MR imaging system main magnets.

The imaging system will have the same elements as a conventional MR imaging system, however, they will function differently. A static magnetic field from a main imaging magnet, shown as 125 in FIGS. 1, 3, should be extremely low (such as 0.1 Tesla) to prevent signals from "stationary" tissue and undesired blood pools contributing to the angiographic image. A small high-field polarization magnet 200 and a large low-field main magnet, instead of a large high-field main magnet will reduce the cost of the system greatly.

Figure 3:
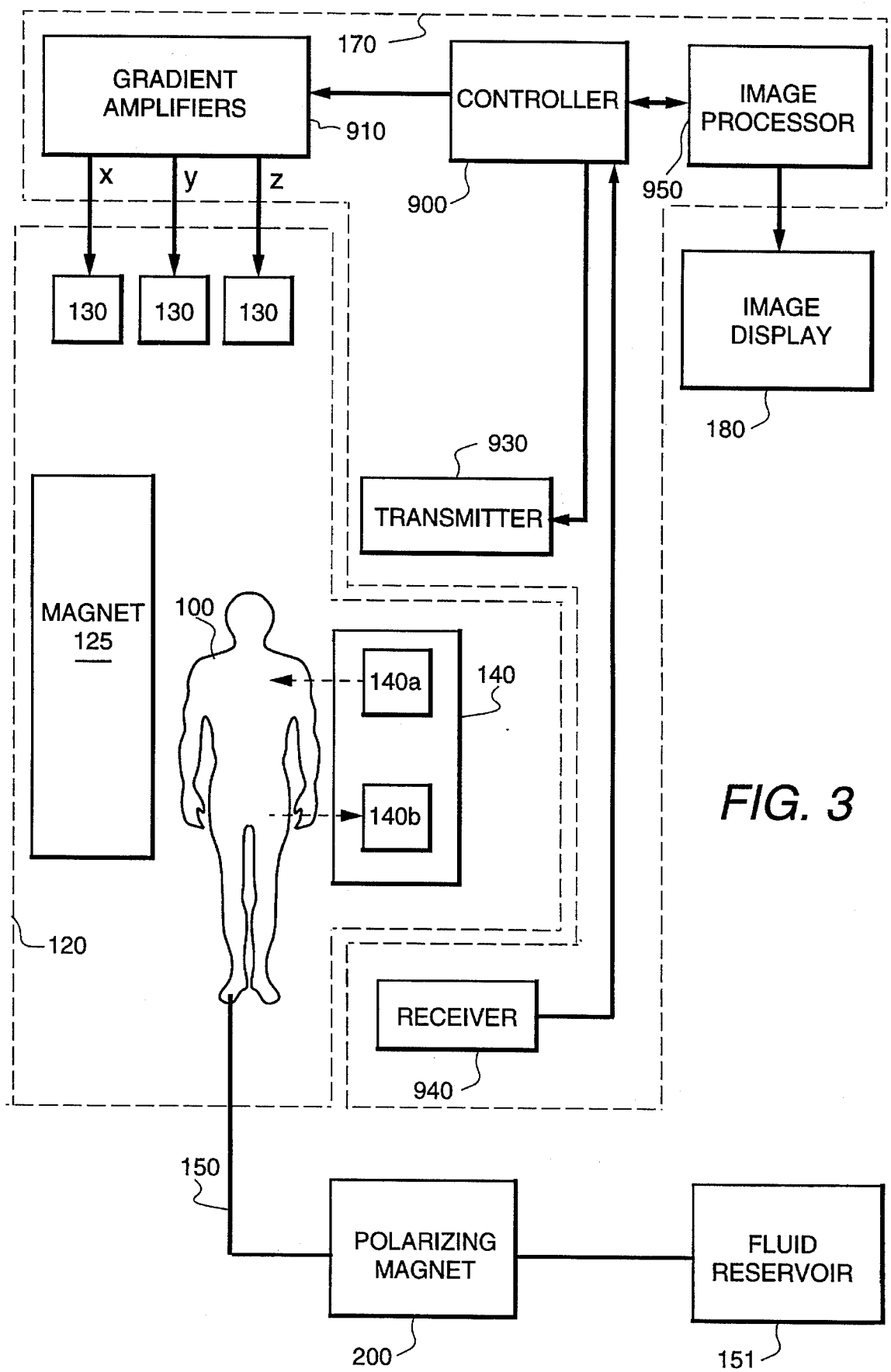
FIG. 3 is a simplified block diagram of a vessel selective MR imaging system suitable for MR angiography according to the present invention.

RF transmitter 930 and RF receiver 940 of the MR system shown in FIG. 3 would be modified to be compatible with the lowfield magnet to resonate at a Larmor frequency corresponding to the strength of magnet 125 (e.g., 4.26 MHz in a 0.1 T magnetic field).

In an alternate embodiment, imaging magnet 125 could be a resistive electromagnet which is driven by an amplifier similar to amplifier 910. Such a system should be able to create a pulsed homogeneous field of 30 Gauss (Larmor frequency=128 KHz). Shielded gradient coil designs may be unnecessary with the present invention employing of a low-field main magnet 125 (although one may still want them to prevent interference with nearby equipment).

RF transmitter 930, and RF coil 140 of the present invention perform the same functions as an RF subsystem of a conventional MR imaging device. Because the Larmor frequency is very low, however, RF coil designs having resonant frequencies comparable to the Larmor frequency will be required. At these lower frequencies, very little RF transmit power will be required, being a further advantage of the present invention.

A controller 900 provides control signals to magnetic field gradient amplifiers 910. These amplifiers drive magnetic field gradient coils 130 situated within the magnet enclosure 120. Gradient coils 130 are capable of generating magnetic field gradients in three mutually orthogonal directions.

Controller 900 generates signals which are supplied to RF transmitter 930 to generate RF pulses at one or more predetermined frequencies and with suitable power to nutate selected spins within RF transmit coil 140a situated within the bore of magnet 125.

MR response signals are sensed by RF receive coil 140b connected to receiver 940. Since the fluid from fluid reservoir 151 has passed through polarizing magnet 200, it acquires a significantly larger longitudinal magnetization, $M_L$, than 'spins' which are only subjected to low-field magnet 125. Consequently, when nutated by the RF pulses, 'spins' which have passed through toroidal polarizing magnet 200 exhibit larger transverse magnetization, $M_L$, and consequently produce a much larger MR response signal. Receiver 940 processes the MR response signals by amplifying, demodulating, filtering and digitizing. Controller 900 also collects the signals from receiver 940 and propagates them to a calculation means 950 where they are processed.

Calculation means 950 applies a Fourier transformation to the signals received from controller 900 to create an MR image. The image created by calculation means 950 is displayed on an image display means 180.

Compared to conventional imaging, the MR response signal of 'spins' which did not pass through toroidal polarizing magnet 200 experience a 0.1 T magnetic field, 15 times lower than that experienced by a conventional 1.5 T MR imaging system. A 10 T toroidal polarizing magnet 200 produces 6.67 times more polarization than a conventional 1.5 T main magnet for fluid 151 which passes through polarization magnet 200. Therefore, the MR signal difference, or contrast, between polarized and non-polarized 'spins' would be on the order of 100 times.

The MR system outlined in FIG. 3 may also be used for the generation of conventional MR images in a manner well known to those skilled in the art. Received MR response signals are detected with either the same RF coil used by the transmitter or a surface coil independent of the coil driven by the transmitter.

While several presently preferred embodiments of the novel MR vascular imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) imaging system for obtaining vessel-selective MR images from a subject comprising:
   a) a low-field imaging magnet for applying a substantially uniform magnetic field over said subject;
   b) a high-field polarizing magnet having a toroidal geometry for polarizing a contrast fluid;
   c) a catheter for routing the polarized contrast fluid from the high-field polarizing magnet into said subject;
   d) an RF transmitter means for transmitting RF energy into said subject of a selected duration, amplitude and frequency to cause nutation of the contrast fluid and other tissue within said subject;
   e) a gradient means for varying the amplitude of the magnetic field in at least one spatial dimension over time;
   f) an RF receive coil for detecting a set of MR response signals from the contrast fluid and other tissue within said subject;
   g) a receiver means coupled to the RF receive coil for receiving the detected MR response signals;
   h) a calculation means for calculating an image from the detected MR response signals;
   i) a controller means connected to the RF transmitter means, the receiver means, the calculation means and the gradient means, for activating the RF transmitter means, the receiver means, the calculation means and the gradient means each according to a predetermined MR pulse sequence; and
   j) a display means connected to the calculation means for displaying the calculated image to an operator.

2. A method of obtaining magnetic resonance (MR) images from a subject comprising:
   a) applying a substantially homogeneous magnetic field over said subject;
   b) polarizing a contrast fluid by passing it through a high-field polarizing magnet having a toroidal shape;
   c) routing the contrast fluid from the polarizing magnet and into a selected vessel of said subject;
   d) transmitting RF energy into said subject of a selected duration, amplitude and frequency to cause nutation of the contrast fluid and other tissue within said subject;
   e) varying the amplitude of the magnetic field in at least one spatial dimension over time;
   f) detecting a set of MR response signals from the contrast fluid and other tissue within said subject;
   g) receiving the detected MR response signals;
   h) calculating an image from the detected MR response signals; and
   i) displaying the calculated image to an operator.

* * * * *